United States Patent [19]

Suzuki et al.

[11] Patent Number: 4,610,674

[45] Date of Patent: Sep. 9, 1986

[54] CATHETER INTRODUCING INSTRUMENT

[75] Inventors: Tatsuo Suzuki, Machida; Atsushi Matsumoto, Fuji, both of Japan

[73] Assignee: Terumo Kabushi Kaisha, Tokyo, Japan

[21] Appl. No.: 770,720

[22] Filed: Aug. 29, 1985

[30] Foreign Application Priority Data

Sep. 13, 1984 [JP] Japan ............................... 59-190487

[51] Int. Cl.⁴ ........................ A61M 25/00; A61M 5/00
[52] U.S. Cl. .................................... 604/282; 604/167
[58] Field of Search ............................. 604/51, 158–170, 604/264, 280–283; 128/348.1, 658

[56] References Cited

U.S. PATENT DOCUMENTS

| | | | |
|---|---|---|---|
| 2,136,050 | 11/1938 | Holden | 285/114 |
| 2,905,178 | 9/1959 | Hilzinger | 128/348.1 X |
| 3,525,339 | 8/1970 | Halligan | 604/264 X |
| 3,802,433 | 4/1974 | Raven | 604/283 |
| 4,044,765 | 8/1977 | Kline | 604/282 X |
| 4,430,083 | 2/1984 | Ganz et al. | 604/283 |

FOREIGN PATENT DOCUMENTS 2065479 7/1981 United Kingdom ............... 604/167

OTHER PUBLICATIONS

Kolobow et al., "A New Thin-Walled Non-Kinking Catheter", Surg. Oct. 1970, vol. 68, No. 4, pp. 625–626.

Primary Examiner—Dalton L. Truluck
Attorney, Agent, or Firm—Frishauf & Partners

[57] ABSTRACT

A catheter introducer includes a hollow sheath extending continuously from a base end portion thereof to a distal end portion thereof, and a hollow hub having a connection portion for connecting the hub to the sheath in such a manner that the hub and sheath partially overlap. A reinforcing coil body is fitted in the connection portion and extends axially of the sheath from the connection portion toward the distal end of the sheath to a point beyond the connection portion. The hub has a valve for enabling a catheter to be passed therethrough under liquid-tight conditions.

15 Claims, 9 Drawing Figures

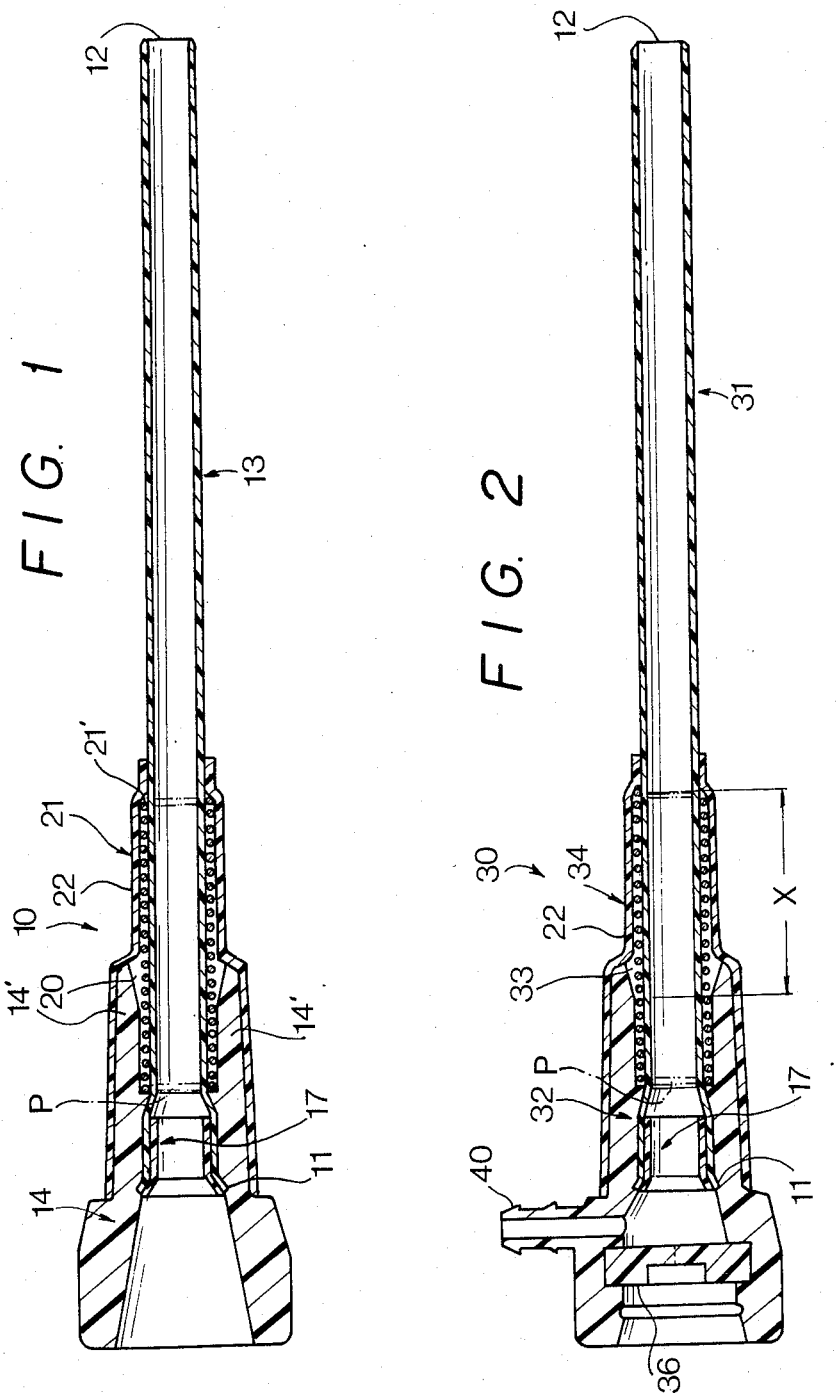

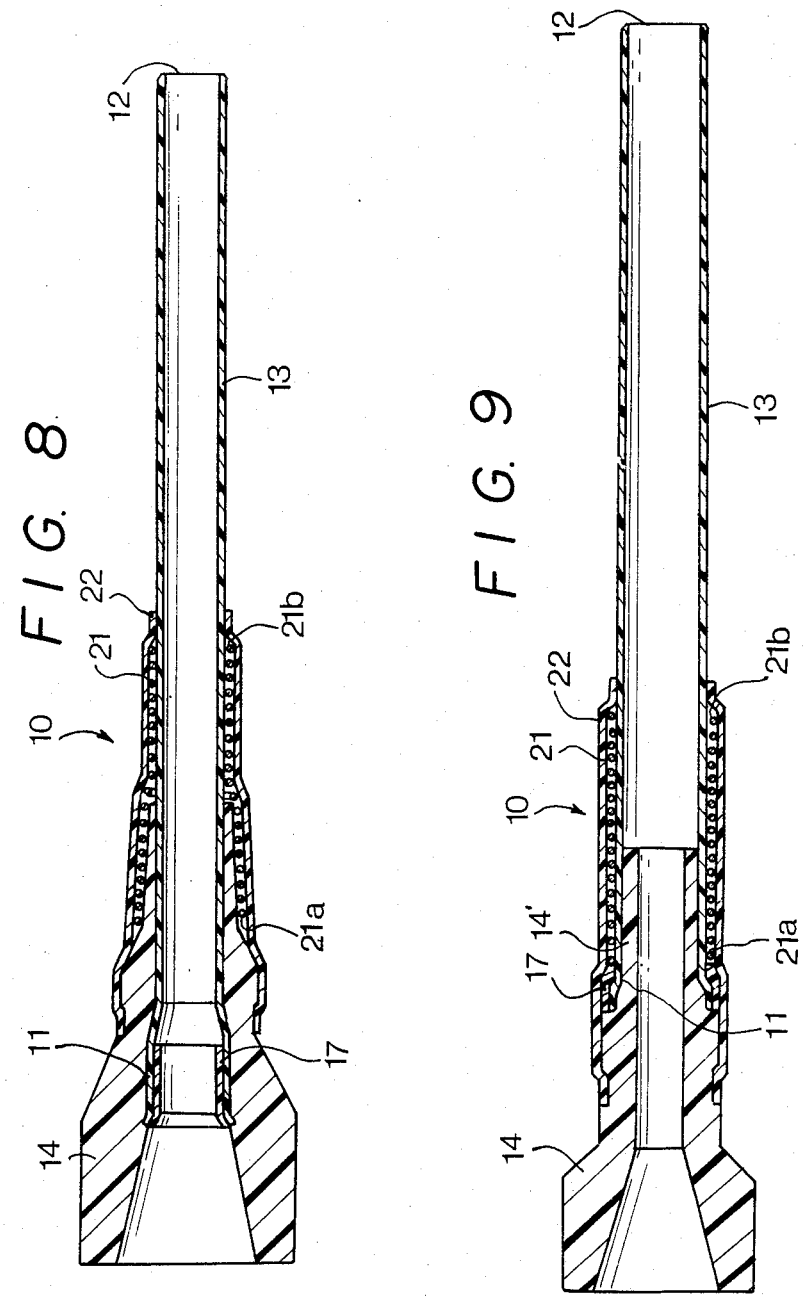

CATHETER INTRODUCING INSTRUMENT

BACKGROUND OF THE INVENTION
1. Field of the Invention

This invention relates to a catheter introducer well-suited for introducing a catheter into a blood vessel.

2. Description of the Prior Art

The conventional catheter introducer includes a sheath having a hollow structure extending continuously from a base end portion to a distal end portion, and a hub having a hollow structure and covered by the base end portion of the sheath. The introducer is used to introduce a catheter into a blood vessel. This is performed first by piercing a blood vessel such as an artery or vein with a Seldinger needle. Next, a guide wire is inserted into the blood vessel by being passed through the Seldinger needle. This is followed by withdrawing the Seldinger needle, leaving the inserted guide wire in place. Next, with a dilater inserted and set, the introducer is inserted into the blood vessel so as to pass over and cover the guide wire. The guide wire and dilater are then withdrawn, leaving the introducer in the blood vessel. A catheter may now be introduced into and withdrawn from the blood vessel by being passed through the introducer residing in the blood vessel. Alternatively, a transfusion line may be connected to the introducer to infuse the patient with a medical or other fluid.

The conventional catheter introducer has a number of disadvantages. Specifically, in a case where a patient is to be continuously infused with a medical or other fluid in a state where the catheter introducer is left in place for an extended period of time (e.g., one week), movements by the patient can cause the sheath to bend into a fold at the junction between the comparatively rigid hub and the sheath, which is comparatively flexible. In actual practice, there are many cases where sustained infusion of medical fluid cannot be carried out satisfactorily due to such bending. In order to prevent such bending of the sheath, a catheter introducer has been developed in which a tube is fitted over the junction between the hub and sheath. While a rigid tube can prevent the sheath from bending into a fold at the hub-sheath junction, the sheath loses overall flexibility, thus subjecting the patient to greater discomfort. If a flexible tube is adopted, on the other hand, the tube exhibits almost no effectiveness in terms of preventing bending of the sheath. A recent catheter introducer includes a sheath a section of which has a bellows-like configuration at the hub-sheath junction to prevent the sheath from bending into a fold. However, since the inner surface of the sheath at the bellows section has a number of indentations rather than being smooth, blood tends to reside in the indentations. This raises the possibility that thrombus will occur.

Another problem with the conventional catheter introducer is leakage of blood when the catheter is inserted into and withdrawn through the introducer left in the blood vessel. Accordingly, there is a requirement for a catheter introducer that is capable of reliably preventing leakage of blood at such times.

SUMMARY OF THE INVENTION

A first object of the present invention is to provide a catheter introducer which is capable of preventing the sheath from bending into a fold without greater patient discomfort and of reliably preventing thrombus at a bending portion, and which is capable of infusing medical and other fluids in a stable manner.

A second object of the present invention is to provide a catheter introducer which is capable of preventing the sheath from bending into a fold without greater patient discomfort and of reliably preventing thrombus at a bending portion, and which is capable of infusing medical and other fluids in a stable manner, and further, which is capable of reliably preventing leakage of blood when a catheter is inserted into or withdrawn from the blood vessel through the introducer left in the blood vessel.

According to the present invention, the first object is attained by providing a catheter introducer comprising a hollow sheath extending continuously from a base end portion thereof to a distal end portion thereof, a hollow hub having a connection portion for connecting the hub to the sheath in such a manner that the hub and the sheath partially overlap, and a coil body fitted into the connection portion, the coil body extending axially of the sheath from the connection portion to a portion of the sheath in the proximity of the connection portion.

According to the present invention, the coil body, which covers the region of the connection between the hub and sheath, extends beyond the connection region to a portion of the sheath in the proximity of the connection region.

Further, according to the present invention, the connection portion of the hub has an opening into which the sheath is inserted, thereby connecting the sheath and the hub together.

According to the present invention, fixing means is provided for fixing the base end portion of the sheath, which is inserted into the connection portion, to the hub, an end portion of the coil body on the side of the hub being situated between an inner surface portion of the hub and an outer surface portion of the sheath.

According to the present invention, the opening in the connection portion has a tapered configuration that widens toward the distal end of the connection portion, the tapered opening defining an annular space that keeps the inner surface portion of the hub out of contact with the coil body, which is situated between the inner surface portion of the hub and the outer surface portion of the sheath.

Further, according to the present invention, the sheath and the hub are connected by fitting the sheath over the outer surface portion of the connection portion of the hub.

According to the present invention, fixing means is provided for fixing the base end portion of the sheath, which is covered by the connection portion, to the hub, an end portion of the coil body on the side of the hub being situated on an outer surface portion of the hub.

According to the present invention, the end portion of the coil body on the side of the hub is situated on a part of the outer surface portion of the sheath covering the outer surface portion of the hub.

According to the present invention, the coil body has a portion which contacts the sheath, the portion having a maximum inner diameter which is no more than about 1.1 times the outer diameter of the sheath.

According to the present invention, the coil body is covered with a heat-shrinkable or elastic tube.

According to the present invention, the hub has a side wall formed to include a medical fluid infusion port communicating with the interior of the hub.

According to the present invention, the second object is attained by providing a catheter introducer comprising a hollow sheath extending continuously from a base end portion thereof to a distal end portion thereof, a hollow hub having a connection portion for connecting the hub to the sheath in such a manner that the hub and the sheath partially overlap, a valve body provided in the hub for enabling a catheter to be passed therethrough under liquid-tight conditions, and a coil body fitted into the connection portion, the coil body extending axially of the sheath from the connection portion to a portion of the sheath in the proximity of the connection portion.

The catheter introducer for attaining the second object of the invention may be provided with the characterizing elements of the first-described catheter introducer. Furthermore, the valve body consists of a flexible, elastic material and has a first end face provided with an elongated first incision and a second end face provided with an elongated second incision, the first and second incisions being formed so as to intersect each other internally of the valve body without passing entirely therethrough.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a sectional view illustrating an embodiment of a catheter introducer according to the present invention;

FIG. 2 is a sectional view illustrating another embodiment of a catheter introducer according to the present invention;

FIGS. 8 and 9 are sectional views illustrating modifications of the catheter introducer shown in FIG. 1.

DESCRIPTION OF THE PREFERRED EMBODIMENTS

Figure 3:
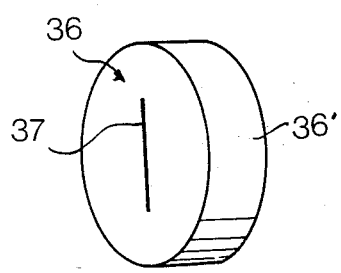
FIGS. 3 and 4 are enlarged perspective views of a valve body included in the embodiment of FIG. 2.

Preferred embodiments of the present invention will now be described with reference to the drawings.

FIG. 1 is a sectional view illustrating an embodiment of a catheter introducer according to the present invention. The catheter introducer, indicated generally at numeral 10, includes a hollow sheath 13 extending continuously from a base end portion 11 to a distal end portion 12, and a hollow hub 14 fitted onto the base end portion 11 of the sheath 13. More specifically, the sheath 13 and hub 14 are connected in a state where the base end portion 11 of the sheath 13 is inserted into a connection portion 14' of the hub 14 that is on the side facing the sheath 13. The base end portion 11 of the sheath 13 so inserted is fixedly secured to the hub 14 by being caulked thereto by a hollow caulking pin 17. A space 20 is defined between the inner surface of the hub 14 and the outer surface of the base end portion 11 of sheath 13. Arranged in the space 20 is a coil body 21 for preventing bending of the sheath 13. As illustrated in FIG. 1, the coil body 21 extends axially of the sheath 13 and has a distal end portion 21' on the side of the sheath 13. The coil body 21 is arranged in the connection portion between the hub 14 and the sheath 13 in such a manner that the distal end portion 21' of the coil body 21 extends from the distal end of the connection portion 14' of hub 14 toward the distal end, of the sheath 13 up to a portion of the sheath 13 at the proximate end of the connection portion 14'.

The sheath 13 consists of a fluoroplastic, ethylene resin, propylene resin or the like. The hub 14 consists of an ethylene resin, propylene resin, amide resin, carbonate resin, styrene resin or the like. The coil body 21 is made of stainless steel, synthetic resin or the like.

Ideally, the coil body 21 has an inner diameter which is no more than 1.1 times the outer diameter of the sheath 13. The reason is that an inner diameter of the coil body 21 greater than 1.1 times that of the outer diameter of sheath 13 would allow the sheath 13 when flexed to deform internally of the coil 21 into an ellipse having a large eccentricity, thereby increasing the likelihood that the sheath will bend into a fold. Accordingly, such bending of the sheath 13 can be reliably prevented by making the inner diameter of the coil body 21 no greater than 1.1 times the outer diameter of the sheath 13. Preferably, the inner surface of the connection portion 14' of hub 14 on the side of the sheath is provided with an annular space 20 so that it will not contact the coil body 21. Provision of the space allows the coil body 21 to limit flexing at a sharp angle at a flex point P. Preferably, the annular space 20 widens toward the open end of the hub 14 on the sheath side 14' and, hence, has a tapered configuration.

The coil body 21 is fixed to a degree that will not allow it to move on the sheath 13. Means for fixing the coil body 21 are a heat-shrinkable tube 22 or an elastic tube, described below, for covering the coil body 21. Such a tube member may be used to fix the inner and outer diameter relationships among the hub 14, sheath 13 and coil body 21. More specifically, the outer diameter of the sheath 13 may be made substantially equal to or smaller than the inner diameter of the coil body 21, and the inner diameter of the hub may be made substantially equal to or smaller than the outer diameter of the coil body 21. Further, an arrangement may be adopted in which the coil body 21 is embraced by the inner surface portion of the hub 14 and the outer surface portion of the sheath 13.

The coil body 21 flexes at the portion thereof that is not fixed and thus prevents the sheath 13 from bending into a fold. Accordingly, if the length X of the non-fixed portion were made too small, there would be instances where the sheath 13 could not be prevented from bending into a fold. Though the length X of the non-fixed portion differs depending upon the diameter of the sheath 13, the preferred length is no less than 5 mm and no more than 20 mm at most. The length of no more than 20 mm is preferred because a greater length would make the portion of the introducer that is not inserted into the body too large, thus making the introducer difficult to handle. The length X most preferred is considered to be from 8 to 15 mm.

The coil body 21 is arranged to project from the connection portion 14' of hub 14 on the side of sheath 13 and is covered by the connection portion 14' of hub 14 and by the heat-shrinkable tube 22. Applying heat to the heat-shrinkable tube 22 causes the tube to shrink, thereby fixing the coil body 21 to and uniting it with the hub 14. This assures that the coil body 21 will not slide out from the space 20. The heat-shrinkable tube 22 is made of polyester, polyethylene or the like. If the heat-shrinkable tube is made of silicone rubber or of a flexible material such as vinyl chloride plastisol, fixing of the coil body 21 can be achieved without any loss in the flexibility of the sheath 13 and coil body 21. A flexible tube which is not heat-shrinkable may also be used.

FIGS. 8 and 9 illustrate modifications of the catheter introducer shown in FIG. 1. Portions similar to those shown in FIG. 1 are designated by like reference characters. In the introducer shown in FIG. 9, the sheath 13 covers the connection portion 14' of hub 14 and is fixedly secured to the hub 14 by being caulked thereto by the hollow caulking pin 17. The coil body 21 is provided in such a manner that the end portion 21a thereof on the side of the hub is situated on the outer surface of the sheath 13 at the portion thereof covering the outer surface of connection portion 14' of hub 14. The end portion 21b of the coil body 21 on the side of the sheath 13 projects beyond the distal end of the connection portion 14' of hub 14 so as to reach a portion of the sheath 13 in the proximity of the connection portion 14'. The end portion 21a of the coil body 21 on the side of the hub 14 may be extended further to reach the rear end of the hub 14 (the part of the hub 14 where the sheath 13 is not present). The coil body 21 is covered by the heat-shrinkable tube 22.

As in the arrangement of FIG. 1, the introducer illustrated in FIG. 8 has the sheath 13 inserted into the open end of the hub 14 and fixedly secured to the hub 14 by the hollow caulking pin 17. This arrangement differs from that of FIG. 1 in that the coil body 21 extends from the outer surface portion of hub 14 onto the terminal side of the sheath 13 beyond the open end of the hub 14. The two embodiments are the same in other respects.

Figure 4:
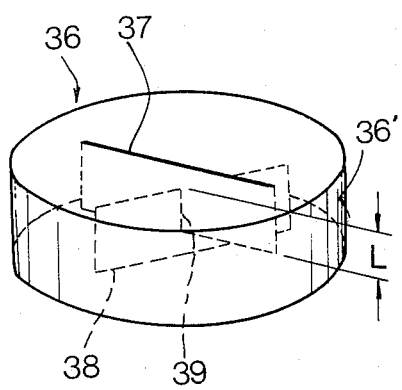

FIG. 2 is a sectional view illustrating another embodiment of the catheter introducer according to the present invention. As in the catheter introducer 10 of the foregoing embodiments, the catheter introducer of the present embodiment, indicated at number 30, includes a sheath 31 and a hub 32 and has a coil body 34 arranged in a space 33 defined between the connected sheath 31 and hub 32. Provided on the inner surface portion of the hub 32 is a valve body 36 through which a catheter is capable of being passed under liquid-tight conditions for preventing leak of blood. As shown in the perspective views of FIGS. 3 and 4, the valve body 36 comprises a body 36' having a first end face provided with an elongated first incision 37 and a second end face provided with an elongated second incision 38. The first and second incisions 37, 38 do not pass entirely through the thickness of the body 36' but intersect internally of the valve body 36' to form an intersection 39 having a length L. This construction allows a catheter to be passed through the first and second incisions 37, 38 and through their intersection 39 as the body 36' undergoes elastic deformation caused by the insertion of the catheter. Accordingly, even if the catheter has a comparatively large outer diameter, the incisions 37, 38 continuously pressure the catheter to prevent the formation of gaps at the periphery thereof as the catheter is passed longitudinally through the valve 36. By forming the valve body 36 of an elastic, flexible material as mentioned above, the incised portions of the body 36' come into substantially liquid-tight surface contact with the periphery of the catheter. The side wall of the hub 32 is provided with a medical fluid infusion port 40 on the side of the valve body 36 facing the sheath 31. The port 40 is connected to a transfusion line to make possible the continuous infusion of a medical fluid.

Discussed next will be the results of experiments for investigating the bending conditions of the catheter introducers 10, 30 of the foregoing embodiments of the present invention. The conventional catheter introducer was subjected to the same experiments and the experimental results were compared with those for the catheter introducers 10, 30.

Experimental Method

Figure 5:
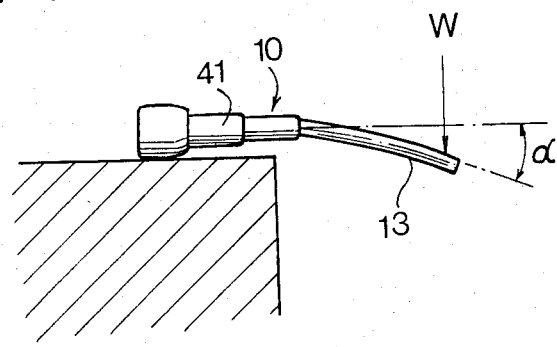
FIG. 5 is a front view of a method of testing the bending of a sheath constituting a catheter introducer.

As shown in FIG. 5, the hub 14 (32) of the catheter introducer 10 (30) was held stationary and a load W was applied to the distal end of the sheath 13 (31) to cause the sheath to flex through an angle $\alpha$ from the horizontal. The angle $\alpha$ was measured.

Samples Compared

A. Embodiment

The catheter introducer used had a sheath with an inner diameter of 2.8 mm and an outer diameter of 3.2 mm, respectively, sheath length of 110 mm, an inner diameter at the inlet of the hub to the clearance of 5 mm, and an inner diameter inside the sheath of 3.8 mm. The coil body had a wire diameter of 0.15 mm, an inner diameter of 3.5 mm and a length of 15 mm. The flexible tube used was a shrinkable tube made of silicone rubber and having an inner diameter of 3 mm following shrinkage.

B. Embodiment

The inner diameter of the coil body was 3.2 mm. The sample was identical with that of Embodiment A in other respects.

C. Embodiment

The inner diameter of the coil body was 3.7 mm. The sample was identical with that of Embodiment A in other respects.

D. Comparative Example (Conventional Catheter Introducer)

The inner and outer diameters of the sheaths were 2.8 mm and 3.1 mm, respectively, sheath length was 110 mm, and there was no clearance at the connection between the sheath and the hub.

E. Comparative Example (Conventional Catheter Introducer)

The inner and outer diameters of the sheaths were 2.8 mm and 3.2 mm, respectively, sheath length was 120 mm, and the sheath-tube junction was covered by a tube having a length of 10 mm.

| Experimental Results | |
|---|---|
| SAMPLE | ANGLE $\alpha$ AT WHICH SHEATH BENT INTO FOLD |
| A | 60° |
| B | 90° or more |
| C | 40° |
| D | 35° |
| E | 35° |

These experimental results demonstrate that the catheter introducer 10 (30) according to the present invention has a bending strength improved over that of the conventional catheter introducer by virtue of the coil body 21 (34). These results also show that folding caused by bending can be prevented with even greater reliability if the inner diameter of the coil body 21 is not more than 1.1 times the outer diameter of the sheath 13.

DETAILED OPERATION OF THE INVENTION

Figure 6:
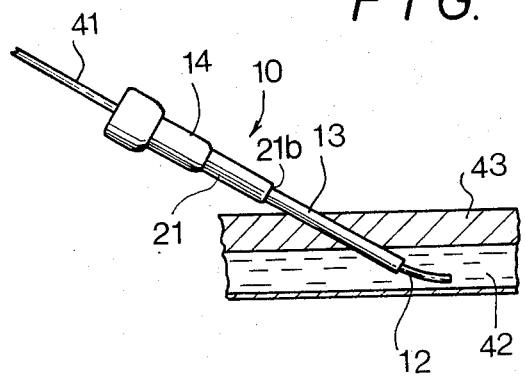
FIG. 6 is a sectional view showing a method of using the catheter introducer of FIG. 1.
Figure 7:
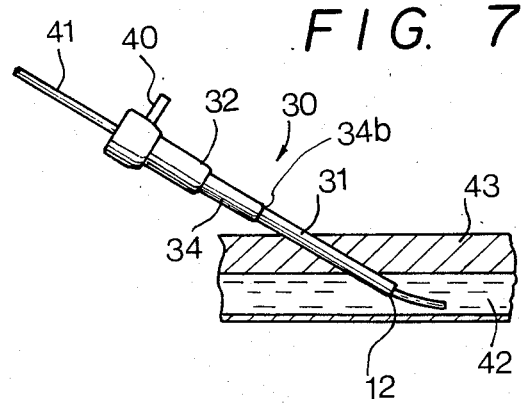
FIG. 7 is a sectional view showing a method of using the catheter introducer of FIG. 2.

The catheter introducers 10, 30 of the above-described embodiments are used in a manner which will now be described. First, a blood vessel such as an artery or vein is pierced with a Seldinger needle. Next, a guide wire is inserted into the blood vessel by being passed through the Seldinger needle. This is followed by withdrawing the Seldinger needle, leaving the inserted guide wire in place. Next, with a dilater inserted and set, the introducer 10 (30) is inserted into the blood vessel so as to pass over and cover the guide wire. The guide wire and dilater are then withdrawn, leaving the introducer 10 (30) in the blood vessel. As shown in FIGS. 6 and 7, a catheter 41 is introduced into and withdrawn from the blood vessel, indicated at 42, by being passed through the introducer 10 (30) residing in the blood vessel. Alternatively, a transfusion line may be connected to the introducer 10 (30) to infuse the patient with a medical or other fluid. Numeral 43 denotes subcutaneous tissue In the above operation, the sheath 13 (31) of the introducer 10 (30) residing in the blood vessel 42 is inserted into the patient's body up to adjacent to the end portion 21b (34b) of the coil body 21 (34) on the sheath side, and the portion of the sheath external to the patient's body is covered by the coil body 21 (34). Therefore, folding of the sheath 13 (31) external to the patient's body due to the patient's movements is prevented by the coil body 21 (34) without subjecting the patient to greater discomfort, thereby enabling the continuous infusion of a medical fluid or the like safely and reliably.

Furthermore, since the inner surface of the sheath 13 (31) is smooth, blood does not reside at any point along the sheath. This makes it difficult for blood to coagulate along the inner surface of the sheath, so that the catheter introducer can be used with safety.

Since the introducer 30 has the valve body 36 serving as a backflow preventing valve, there is no leakage of blood caused by backflow of the blood from the hub 32 when the catheter 41 is inserted and withdrawn through the introducer residing in the blood vessel. This feature also allows the introducer to be used with safety.

In addition, since the introducer 30 is equipped in its side wall with the medical fluid infusion port 40, continuous infusion is made possible by connecting the port 40 with a transfusion line.

EFFECTS OF THE INVENTION

Thus, as set forth above, the catheter introducer embodied in FIG. 1 comprises a hollow sheath extending continuously from a base end portion thereof to a distal end portion thereof, a hollow hub having a connection portion for connecting the hub to the sheath in such a manner that the hub and the sheath partially overlap, and a coil body fitted into the connection portion, the coil body extending axially of the sheath from the connection portion to a portion of the sheath in the proximity of the connection portion. This makes it possible to prevent the sheath from bending into a fold without increased patient discomfort. As a result, thrombus that might otherwise be caused by such bending of the sheath can be reliably prevented, and medical fluid can be infused into the patient's blood vessel in stable fashion.

The coil body, which covers the region of the connection between the hub and sheath, extends beyond the connection region to a portion of the sheath in the proximity of the connection region. This enables the hub, sheath and coil body to be integrated reliably, thereby making it possible to positively prevent the sheath portion from being bent into a fold.

Further, the connection portion of the hub has an opening into which the sheath is inserted, whereby the sheath and the hub are interconnected. This makes it easy to effect the connection.

In addition, fixing means is provided for fixing the base end portion of the sheath, which is inserted into the connection portion, to the hub, an end portion of the coil body on the side of the hub being situated between an inner surface portion of the hub and an outer surface portion of the base end portion of the sheath. As a result, the hub, sheath and coil body can be integrated reliably, thereby making it possible to positively prevent the sheath portion from being bent into a fold.

Further, the opening in the connection portion has a tapered configuration that widens toward the distal end of the connection portion, the tapered opening defining an annular space that keeps the inner surface portion of the hub out of contact with the coil body, which is situated between the inner surface portion of the hub and the outer surface portion of the sheath. The coil body therefore limits bending at a sharp angle.

Further, the sheath and the hub are connected by fitting the sheath over the outer surface portion of the connection portion of the hub. This facilitates the connecting operation.

Further, fixing means is provided for fixing the base end portion of the sheath, which is covered by the connection portion, to the hub, an end portion of the coil body on the side of the hub being situated on an outer surface portion of the hub and, further, on an outer surface portion of the sheath. This enables the hub, sheath and coil body to be integrated reliably, thereby making it possible to positively prevent the sheath portion from being bent into a fold.

Further, the coil body has a portion which contacts the sheath, the portion having a maximum inner diameter which is no more than about 1.1 times the outer diameter of the sheath. This makes it possible to prevent the part of the sheath protruding from the patient's body from bending into a fold over a greater angle of flexure.

Further, the coil body is covered with a heat-shrinkable tube to eliminate any risk of the coil body slipping out. This enables the catheter introducer to be used with greater safety and reliability.

Also, the hub has a side wall formed to include a medical fluid infusion port communicating with the interior of the hub, thereby enabling the continuous infusion of medical fluid.

The catheter introducer embodied in FIG. 2 comprises a a hollow sheath extending continuously from a base end portion thereof to a distal end portion thereof, a hollow hub having a connection portion for connecting the hub to the sheath in such a manner that the hub and the sheath partially overlap, a valve body provided in the hub for enabling a catheter to be passed therethrough under liquid-tight conditions, and a coil body fitted into the connection portion, the coil body extending axially of the sheath from the connection portion to a portion of the sheath in the proximity of the connection portion. This arrangement prevents the sheath from bending into a fold without greater patient discomfort, reliably prevents thrombus at a bending portion, enables medical and other fluids to be infused in a stable manner, and reliably prevents leakage of blood when the catheter introducer is introduced.

The characterizing constituents of the embodiment of FIG. 2 bring forth the actions and effects described above in connection with the embodiment of FIG. 1. In addition, according to the embodiment of in FIG. 2, the valve body consists of a flexible, elastic material and has a first end face provided with an elongated first incision and a second end face provided with an elongated second incision, the first and second incisions being formed so as to intersect each other internally of the valve body without passing entirely therethrough. Such an arrangement makes it possible to reliably prevent the leakage of blood when inserting the catheter.

As many apparently widely different embodiments of the present invention can be made without departing from the spirit and scope thereof, it is to be understood that the invention is not limited to the specific embodiments thereof except as defined in the appended claims.

What is claimed is:

1. A catheter introducer, comprising:
   a hollow sheath extending continuously from a base end portion thereof to a distal end portion thereof;
   a hollow hub having an opening in a connection portion into which said base end portion of said sheath is received, said opening defining an annular space between an inner surface portion of said hub and an outer surface portion of said sheath;
   a coil body mounted in said connection portion of said hub, said coil body extending axially of said sheath from the connection portion to a portion of said sheath in the proximity of the connection portion; and
   fixing means for fixing said base end portion of said sheath, which is received in said connection portion, to said hub, said coil body having an end portion on the side of said hub which is situated between the inner surface portion of said hub and the outer surface portion of said sheath.

2. The catheter introducer according to claim 1, wherein the opening in the connection portion has a tapered configuration that widens toward a distal end of the connection portion, said opening of the tapered configuration defining an annular space that keeps the inner surface portion of said hub out of contact with coil body, which is situated between the inner surface portion of said hub and said outer surface portion of said sheath.

3. The catheter introducer according to claim 1, wherein said coil body has a portion which contacts said sheath, said portion of the coil body having a maximum inner diameter which is no more than about 1.1 times the outer diameter of said sheath.

4. The catheter introducer according to claim 3, wherein the portion of said coil body that contacts said sheath has a minimum inner diameter which is approximately equal to that of the outer diameter of said sheath.

5. The catheter introducer according to claim 1, wherein said coil body is covered with a heat-shrinkable tube.

6. The catheter introducer according to claim 1, wherein said coil body is covered with an elastic tube.

7. The catheter introducer according to claim 1, wherein said hub has a side wall formed to include a medical fluid infusion port communicating with the interior of said hub.

8. A catheter introducer, comprising:
   a hollow sheath extending continuously from a base end portion thereof to a distal end portion thereof;
   a hollow hub having an opening in a connection portion into which said sheath is received, said opening defining an annular space between an inner surface portion of said hub and an outer surface portion of said sheath;
   a valve body provided in the hub for enabling a catheter to be passed therethrough under liquid-tight conditions;
   a coil body mounted to said connection portion of said hub, said coil body extending axially of said sheath from the connection portion to a portion of said sheath in the proximity of the connection portion; and
   fixing means for fixing said base end portion of said sheath, which is received in said connection portion, to said hub, said coil body having an end portion on the side of said hub which is situated between the inner surface portion of said hub and the outer surface portion of said sheath.

9. The catheter introducer according to claim 8, wherein the opening in the connection portion has a tapered configuration that widens toward a distal end of the connection portion, said opening of the tapered configuration defining an annular space that keeps the inner surface portion of said hub out of contact with said coil body, which is situated between the inner surface portion of said hub and said outer surface portion of said sheath.

10. The catheter introducer according to claim 8, wherein said coil body has a portion which contacts said sheath, said portion of the coil body having a maximum inner diameter which is no more than about 1.1 times the outer diameter of said sheath.

11. The catheter introducer according to claim 10, wherein the portion of said coil body that contacts said sheath has a minimum inner diameter which is approximately equal to that of the outer diameter of said sheath.

12. The catheter introducer according to claim 8, wherein said coil body is covered with a heat-shrinkable tube.

13. The catheter introducer according to claim 8, wherein said coil body is covered with an elastic tube.

14. The catheter introducer according to claim 8, wherein said hub has a side wall formed to include a medical fluid infusion port communicating with the interior of said hub.

15. The catheter introducer according to claim 8, wherein said valve body consists of a flexible, elastic material and has a first end face provided with an elongated first incision and a second end face provided with an elongated second incision, said first and second incisions being formed so as to intersect each other internally of the valve body without passing entirely therethrough.

* * * * *